(12) United States Patent
Kurome et al.

(10) Patent No.: US 7,442,683 B2
(45) Date of Patent: Oct. 28, 2008

(54) CYCLIC PEPTIDE

(75) Inventors: Toru Kurome, Kusatsu (JP); Naoyuki Awazu, Ritto (JP); Kazutoh Takesako, Otsu (JP); Ikunoshin Kato, Uji (JP)

(73) Assignee: Takara Bio Inc., Shiga (JP)

( * ) Notice: Subject to any disclaimer, the term of this patent is extended or adjusted under 35 U.S.C. 154(b) by 711 days.

(21) Appl. No.: 10/470,918

(22) PCT Filed: Feb. 14, 2002

(86) PCT No.: PCT/JP02/01221

§ 371 (c)(1), (2), (4) Date: Aug. 1, 2003

(87) PCT Pub. No.: WO02/066499

PCT Pub. Date: Aug. 29, 2002

(65) Prior Publication Data

US 2004/0063625 A1    Apr. 1, 2004

(30) Foreign Application Priority Data

Feb. 19, 2001   (JP) .............................. 2001-041615

(51) Int. Cl.
*A61K 38/12*   (2006.01)

(52) U.S. Cl. ........................................ 514/11; 530/317

(58) Field of Classification Search ....................... None
See application file for complete search history.

(56) References Cited

U.S. PATENT DOCUMENTS

| | | | |
|---|---|---|---|
| 4,401,656 A * | 8/1983 | Failli et al. | ..................... 514/11 |
| 4,409,210 A | 10/1983 | Kawaguchi et al. | |
| 4,533,631 A | 8/1985 | Kawaguchi et al. | |
| 5,171,836 A * | 12/1992 | Yoshida et al. | ............... 530/317 |
| 5,830,855 A * | 11/1998 | Takemoto | ..................... 514/11 |

FOREIGN PATENT DOCUMENTS

| | | |
|---|---|---|
| DE | 199 33 173 A 1 | 1/2001 |
| EP | 0 084 826 | 8/1983 |
| JP | 3127798 A | 5/1991 |
| JP | 5279384 A | 10/1993 |
| WO | WO 95/30692 | 11/1995 |
| WO | 0105815 A1 | 1/2001 |

OTHER PUBLICATIONS

Jamison, James et al., "Syntheses and Antifungal Activity of Pseudomycin Side-Chain Analogues. Part I.", *Bioorganic & Medicinal Chemistry Letters*, vol. 10, No. 18, Sep. 18, 2000, p. 2101-2105 XP004208321.

* cited by examiner

*Primary Examiner*—Christopher R. Tate
*Assistant Examiner*—Roy Teller
(74) *Attorney, Agent, or Firm*—Browdy and Neimark PLLC

(57) ABSTRACT

A novel cyclic peptide having an antifungal activity, its pharmacologically acceptable salts and antifungal medicinal compositions containing the same.

3 Claims, 1 Drawing Sheet

CYCLIC PEPTIDE

TECHNICAL FIELD

The present invention relates to a novel cyclic peptide having an antifungal activity and a pharmacologically acceptable salt thereof as well as an antifungal pharmaceutical composition containing the same.

BACKGROUND ART

Fungi infect man, animals, plants and the like to cause various diseases. Among these, fungi belonging to the genus *Candida*, the genus *Cryptococcus*, the genus *Aspergillus* and the like are known as the principal causative fungi of systemic mycoses.

Currently known antifungal agents that can be used for treatment or prevention of fungal infections are only a very few. The therapeutic drugs available for systemic mycoses in man and animals are amphotericin B, flucytosine, miconazole and fluconazole. However, therapeutic activities of these agents are unsatisfactory, either in efficacies, toxicities, antimicrobial spectra and the like.

Specifically, few agents are effective for fungi belonging to the genus *Aspergillus* among fungi that cause systemic mycoses in man (e.g., *Candida albicans*, *Cryptococcus neoformans* and *Aspergillus fumigatus*). Therefore, a therapeutic agent that can cover the drawbacks associated with the conventional agents has been desired.

OBJECTS OF INVENTION

The main object of the present invention is to provide a novel cyclic peptide having an excellent antifungal activity among cyclic lipopeptides having D-allo-threonine or various D-α-amino acids having β-hydroxy that can be obtained by chemical synthesis.

SUMMARY OF INVENTION

In summary, the present invention relates to a cyclic peptide of general Formula (1) or a pharmaceutically acceptable salt thereof:

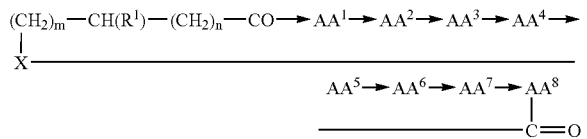

wherein
m and n may be identical or different from each other, and are independently 0 or 1;
X is O or NH;
$R^1$ is hydrogen, C6-21 alkyl, substituted alkyl, alkenyl, substituted alkenyl, acylamino, aryl, substituted aryl, heterocyclic ring or substituted heterocyclic ring, wherein said substituted alkyl, substituted alkenyl, substituted aryl or substituted heterocyclic ring is substituted with at least one of hydroxyl group, C1-8 alkyl, C1-8 alkoxy, C2-8 alkenyl, C2-8 acyl, C2-8 acyloxy, C6-14 aryl, C6-14 aryloxy or C1-8 heterocyclic ring;
$AA^1$ to $AA^6$ are independently an α- or β-amino acid;
$AA^7$ is a D-α-amino acid having HO— in a side chain; and
$AA^8$ is an α- or β-amino acid.

The present inventors have searched novel cyclic lipopeptides prepared by means of chemical synthesis for a compound having a strong activity on fungi that cause systemic mycoses in humans (e.g., *Candida albicans*, *Cryptococcus neoformans* and *Aspergillus fumigatus*). As a result, the present inventors have unexpectedly found that, among cyclic lipopeptides each consisting of eight α- or β-amino acid residues and one fatty acid residue having hydroxy group or amino group at the α- or β-position, a cyclic lipopeptide compound containing at least one D-α-amino acid residue having β-hydroxy, preferably D-α-amino acid having erythro form β-hydroxy, or D-allo-threonine exhibits a strong activity on the above-mentioned fungi (including *Aspergillus fumigatus*) that cause systemic mycoses in humans for which few agents have been effective. Thus, the present invention has been completed.

DETAILED DESCRIPTION OF THE INVENTION

Figure 1:
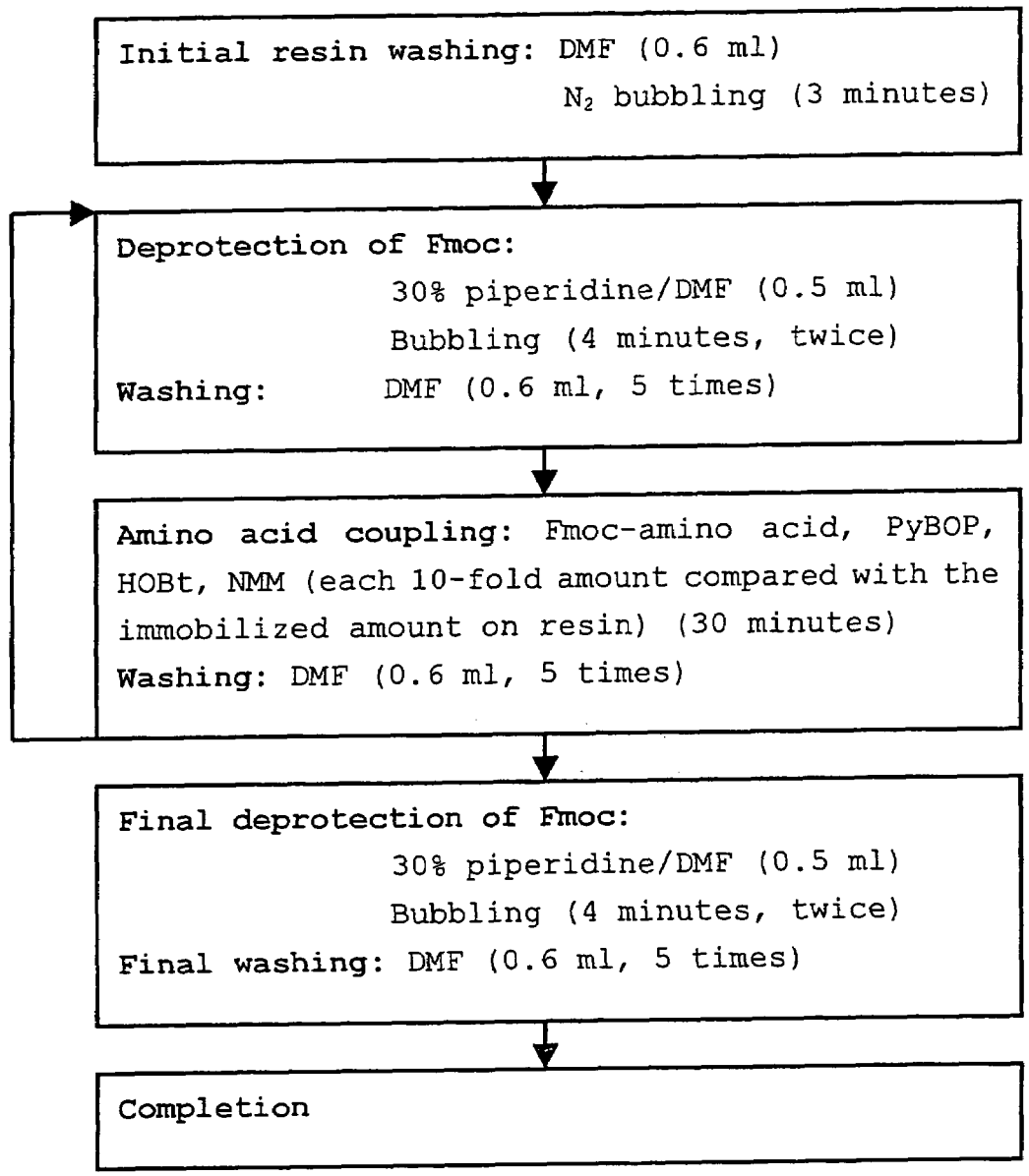
FIG. 1: a FIGURE illustrating a general protocols of solid phase synthesis according to the present invention.

The compound of Formula (1) is a cyclic lipopeptide consisting of one hydroxy acid or amino acid residue having $R^1$ as a lipid portion as well as eight α- or β-amino acid residues, $AA^1$ to $AA^8$, wherein m and n may be identical or different from each other, and are independently 0 or 1; and X is O or NH.

Said $R^1$ is hydrogen, C6-21 alkyl, substituted alkyl, alkenyl, substituted alkenyl, acylamino, aryl, substituted aryl, heterocyclic ring or substituted heterocyclic ring.

The substituted alkyl, substituted alkenyl, substituted aryl or substituted heterocyclic ring is substituted with at least one of hydroxyl group, C1-8 alkyl, C1-8 alkoxy, C2-8 alkenyl, C2-8 acyl, C2-8 acyloxy, C6-14 aryl, C6-14 aryloxy or C1-8 heterocyclic ring.

Preferable alkyl for $R^1$ is exemplified by C6-21 linear or branched alkyl such as $CH_3(CH_2)_5$—, $cycloC_6H_{11}CH_2$—, $CH_3(CH_2)_6$—, $CH_3(CH_2)_7$—, $CH_3(CH_2)_8$—, $CH_3(CH_2)_9$—, $CH_3(CH_2)_{10}$—, $CH_3(CH_2)_{11}$—, $CH_3(CH_2)_{12}$—, $CH_3(CH_2)_{13}$—, $CH_3(CH_2)_{11}CH(CH_3)$—, $CH_3(CH_2)_{14}$—, $CH_3(CH_2)_{15}$—, $CH_3(CH_2)_{16}$—, $CH_3(CH_2)_{17}$—, $CH_3(CH_2)_{18}$—, $CH_3(CH_2)_{19}$— or $CH_3(CH_2)_{20}$—.

$CH_3(CH_2)_{12}$— and $CH_3(CH_2)_{11}CH(CH_3)$— are preferable. Hydroxy acids having the former and the latter (wherein m is 0 and n is 1) are 3-hydroxy-hexadecanoic acid and 3-hydroxy-4-methyl-hexadecanoic acid, respectively.

Preferable alkenyl for $R^1$ is exemplified by C6-21 linear or branched alkenyl such as $CH_3(CH_2)_4CH=CH—(CH_2)_2$— or $CH_3(CH_2)_5CH=CH(CH_2)_4CH=CH(CH_2)_3$—.

Preferable acyl portion of acylamino for $R^1$ is exemplified by C6-21 linear or branched aliphatic acyl or aromatic acyl such as $CH_3(CH_2)_4CO$—, $CH_3(CH_3)CH(CH_2)_2CO$—, $CH_3(CH_2)_5CO$—, $cycloC_6H_{11}CH_2CO$—, $CH_3(CH_2)_6CO$—, $CH_3(CH_2)_7CO$—, $CH_3(CH_2)_8CO$—, $CH_3(CH_2)_9CO$—, $CH_3(CH_2)_{10}CO$—, $CH_3(CH_2)_{11}CO$—, $CH_3(CH_2)_{12}CO$—, $CH_3(CH_2)_{13}CO$—, $CH_3(CH_2)_{14}CO$—, $CH_3(CH_2)_{15}CO$—, $CH_3(CH_2)_{16}CO$—, $CH_3(CH_2)_{17}CO$—, $CH_3(CH_2)_{18}CO$—, $CH_3(CH_2)_{19}CO$—, $C_6H_5CO$—, $C_6H_5—C_6H_4CO$— or $C_{12}H_7CO$—.

Preferable aryl for $R^1$ is exemplified by phenyl, mesityl, tolyl, naphtyl or anthryl.

Preferable heterocyclic ring for $R^1$ is exemplified by a group such as furil, thienyl, pyrazolyl, imidazolyl, tetrazolyl, thiazolyl, thiadiazolyl or isooxazolyl.

One having hydroxyl group as a substituent is exemplified by $CH_3(CH_2)_{11}C(OH)(CH_3)-$. Hydroxy acid having the same (wherein m is 0 and n is 1) is 3,4-dihydroxy-4-methyl-hexadecanoic acid.

Preferable alkyl, or alkyl portion of alkoxy, as a substituent is exemplified by C1-8 linear or branched alkyl such as $CH_3-$, $CH_3CH_2-$, $CH_3(CH_2)_2-$, $CH_3(CH_2)_3-$, $CH_3(CH_3)CHCH_2-$, $CH_3(CH_2)_4-$, $CH_3(CH_3)CH(CH_2)_2-$, $CH_3(CH_2)_5-$, $cycloC_6H_{11}CH_2-$, $CH_3(CH_2)_6-$ or $CH_3(CH_2)_7-$.

Preferable alkenyl as a substituent is exemplified by C2-8 linear or branched alkenyl such as $CH_2=CHCH_2-$, $CH_2=CH(CH_2)_3-$ or $CH_2=CHCH_2-$.

Preferable aryl, or aryl portion of aryloxy, as a substituent is exemplified by C6-14 aryl such as phenyl, mesityl, tolyl, naphtyl or anthryl. These aryl may have at least one group selected from C1-8 linear or branched alkyl, halogen (e.g., fluoro, chloro, bromo or iodo), hydroxy or above-mentioned aryl.

Preferable acyl, or acyl portion of acyloxy, as a substituent is exemplified by C2-8 linear or branched aliphatic acyl or aromatic acyl such as $CH_3CO-$, $CH_3CH_2CO-$, $CH_3(CH_2)_2CO-$, $CH_3(CH_2)_3CO-$, $CH_3(CH_3)CHCH_2CO-$, $CH_3(CH_2)_4CO-$, $CH_3(CH_3)CH(CH_2)_2CO-$, $CH_3(CH_2)_5CO-$, $cycloC_6H_{11}CH_2CO-$, $C_6H_5CO-$, $C_6H_5-C_6H_4CO-$ or $C_{12}H_7CO-$.

Preferable heterocyclic ring as a substituent is exemplified by C1-8 heterocyclic ring such as a group selected from furil, thienyl, pyrazolyl, imidazolyl, tetrazolyl, thiazolyl, thiadiazolyl or isooxazolyl.

Said $AA^1$ is an α- or β-amino acid having C1-7 linear or branched alkyl group in a side chain, preferably alanine (which has $CH_3-$).

Said $AA^2$ is an α- or β-amino acid having C1-7 linear or branched alkyl group substituted with amino group, preferably ornithine (which has $H_2N-(CH_2)_3-$) or lysine (which has $H_2N-(CH_2)_4-$).

Said $AA^3$ is an amino acid having hydrogen or C1-7 linear or branched alkyl group, or an amino acid having H— or C1-7 linear or branched alkyl group having HO—, HOOC— or $H_2NOC-$, preferably glycine (which has H—), alanine (which has $CH_3-$), serine (which has $HO-CH_2-$), threonine (which has $CH_3CH(OH)-$), glutamic acid (which has $HOOC-(CH_2)_2-$), aspartic acid (which has $HOOC-CH_2-$), glutamine (which has $H_2NOC-(CH_2)_2-$) or asparagine (which has $H_2NOC-CH_2-$). Alternatively, $AA^3$ is β-alanine.

Said $AA^4$ is an amino acid having C1-7 linear or branched alkyl group substituted with hydroxyl group, preferably serine (which has $HO-CH_2-$) or threonine (which has $CH_3CH(OH)-$).

Said $AA^5$ is an amino acid having C1-7 linear or branched alkyl group substituted with hydroxyl group, preferably serine (which has $HO-CH_2-$) or threonine (which has $CH_3CH(OH)-$).

Said $AA^6$ is an amino acid having C1-7 linear or branched alkyl group having $H_2NOC-$, preferably glutamine (which has $H_2NOC-(CH_2)_2-$) or asparagine (which has $H_2NOC-CH_2-$).

Said $AA^7$ is a D-amino acid having C1-7 linear or branched alkyl group substituted with hydroxyl group, preferably D-allo-threonine (which has $CH_3CH(OH)-$) or D-β-hydroxyvaline (which has $CH_3(CH_3)C(OH)-$).

Said $AA^8$ is an α- or β-amino acid having hydrogen or C1-7 linear or branched alkyl group, or an amino acid having C1-7 linear or branched alkyl group substituted with hydroxyl group, preferably glycine (which has H—), alanine (which has $CH_3-$) or threonine (which has $CH_3CH(OH)-$).

Typical examples of the novel cyclic peptides represented by Formula (1') of the present invention include the compounds as shown in Table 1:

Formula (1'):

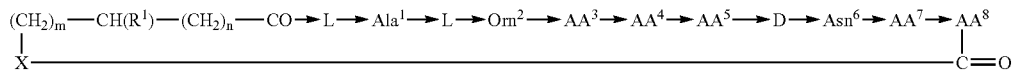

TABLE 1

| | $R_1$ | X | m, n | $AA^3$ | $AA^4$ | $AA^5$ | $AA^7$ | $AA^8$ |
|---|---|---|---|---|---|---|---|---|
| 1 | $CH_3(CH_2)_{12}-$ | O | 0, 1 | βAla | L-Ser | L-Ser | D-alloThr | Gly |
| 2 | $CH_3(CH_2)_{12}-$ | O | 0, 1 | L-Ala | L-Ser | L-Ser | D-alloThr | Gly |
| 3 | $CH_3(CH_2)_{12}-$ | O | 0, 1 | L-Asn | L-Ser | L-Ser | D-alloThr | Gly |
| 4 | $CH_3(CH_2)_{12}-$ | O | 0, 1 | L-Asp | L-Ser | L-Ser | D-alloThr | Gly |
| 5 | $CH_3(CH_2)_{12}-$ | O | 0, 1 | L-Glu | L-Ser | L-Ser | D-alloThr | Gly |
| 6 | $CH_3(CH_2)_{12}-$ | O | 0, 1 | Gly | L-Ser | L-Ser | D-alloThr | Gly |
| 7 | $CH_3(CH_2)_{12}-$ | O | 0, 1 | L-Ser | L-Ser | L-Ser | D-alloThr | Gly |
| 8 | $CH_3(CH_2)_{12}-$ | O | 0, 1 | βAla | L-Ser | L-Ser | D-alloThr | D-alloThr |
| 9 | $CH_3(CH_2)_{12}-$ | O | 0, 1 | D-alloThr | L-Ser | L-Ser | D-alloThr | Gly |
| 10 | $CH_3(CH_2)_{12}-$ | O | 0, 1 | D-alloThr | L-Ser | L-Ser | D-alloThr | D-alloThr |
| 11 | $CH_3(CH_2)_{12}-$ | O | 0, 1 | βAla | D-alloThr | L-Ser | D-alloThr | Gly |
| 12 | $CH_3(CH_2)_{12}-$ | O | 0, 1 | βAla | L-Ser | D-alloThr | D-alloThr | Gly |
| 13 | $CH_3(CH_2)_{12}-$ | O | 0, 1 | βAla | L-Ser | L-Ser | D-βHOVal | Gly |
| 14 | $CH_3(CH_2)_{12}-$ | O | 0, 1 | βAla | L-Ser | L-Ser | D-βHOPhe | Gly |
| 15 | $CH_3(CH_2)_{10}CONH-$ | O | 1, 0 | βAla | L-Ser | L-Ser | D-alloThr | Gly |
| 16 | $CH_3(CH_2)_{10}CO_2CH_2-$ | NH | 1, 0 | βAla | L-Ser | L-Ser | D-alloThr | Gly |

A D-α-amino acid residue having β-hydroxy can be introduced into the compound of the present invention according to a method in which an amino acid having β-hydroxy which has been introduced beforehand is used as a material, or a method in which β-hydroxy is introduced into a cyclic peptide which has been synthesized such that β-hydroxy can be introduced thereafter. In either case, a compound of interest can be prepared, for example, using an aldol condensation reaction between one selected from various aldehydes or ketones and a glycine residue or the like.

If the introduction of β-hydroxy is carried out by preparing a D-α-amino acid having β-hydroxy, for example, Boc-Gly-OBzl or Fmoc-Gly-OBzl can be used as a material, and one selected from various aldehydes or ketones (acetaldehyde, acetone, etc.) can be used as an electrophilic agent to be reacted with the material. For example, a D-α-amino acid having β-hydroxy can be prepared according to a method in which Fmoc-Gly-OBzl is reacted with a strong base, lithium diisopropylamide (LDA), in an aprotonic solvent (e.g., THF) in the presence of a metal salt (e.g., lithium chloride) to convert Fmoc-Gly-OBzl into a lithium enolate form; or a method in which Fmoc-Gly-OBzl which has been converted into a silyl enol ether form using trimethylsilyl chloride is stirred with an excess amount of an aldehyde or a ketone as an electrophilic agent for several hours at a low temperature. Alternatively, a cyclic peptide that has a residue such as glycine or β-alanine and in which functional groups of constituting amino acids side chain are protected can be prepared, and then glycine or β-alanine residue is converted into a desired β-hydroxy-α-amino acid residue by the reaction as described above. Preferably, the preparation is carried out by conversion of glycine or β-alanine residue into the lithium enolate form using a strong base such as LDA followed by a reaction with an aldehyde or a ketone.

Aprotonic solvents that can be used include dichloromethane and ethyl ether in addition to THF. Metal salts that can be used include magnesium chloride, cesium chloride, titanium chloride, aluminum chloride and a boride in addition to lithium chloride. By appropriately selecting the above to control the stereochemistry of asymmetric center, it is possible to obtain a mixture of diastereomers at an appropriate ratio generated due to an asymmetric carbon newly resulted in a reaction product, or the only desired one of the diastereomers with high yield. Strong bases that can be used for generating a metal enolate include methyllithium and $(n-Bu)_2BOSO_2CF_3$ in addition to LDA. Furthermore, it is important to control the reaction temperature in order to obtain the desired stereochemically pure product. The reaction is usually carried out at a low temperature of −80° C. to −20° C.

The desired compound can be obtained as a single optically active substance or a mixture of diastereomers by purifying the reaction mixture using reverse phase high performance liquid chromatography or the like. The desired compound can be obtained by removal, according to a known method or application thereof, of protecting groups used for the functional groups of constituting amino acids side chain and the functional groups on the aldehyde or the ketone used as a material.

The compound of the present invention can be prepared according to a total synthesis utilizing a liquid phase synthetic method or a solid phase synthetic method.

In either of the synthetic methods, a method for cyclizing a linear peptide (e.g., one represented by general formula (2) can be preferably utilized. A method in which two or three peptide fragments are synthesized and then condensed each other is desirable in order to prepare such a linear peptide via a total synthesis utilizing a liquid phase synthetic method. Various linear peptides can be conveniently prepared also via a total synthesis utilizing a solid phase synthetic method.

$$H\text{-}AA^1\rightarrow AA^2\rightarrow AA^3\rightarrow AA^4\rightarrow AA^5\rightarrow AA^6\rightarrow AA^7\rightarrow AA^8\text{-}O\text{---}(CH_2)_m\text{-}CH(R^1)\text{---}(CH_2)_n\text{-}CO_2H \quad \text{Formula (2):}$$

The total synthesis utilizing a solid phase synthetic method is described with respect to Compound 1 represented by Formula (3) which is an example of a compound of general Formula (1) wherein m=0; n=1, $R_1$ is $CH_3(CH_2)_{12}$—; $AA^1$ is L-Ala; $AA^2$ is L-Orn; $AA^3$ is β-Ala; $AA^4$ is L-Ser; $AA^5$ is L-Ser; $AA^6$ is D-Asn; $AA^7$ is D-allo-Thr; and $AA^8$ is Gly.

Cyclo[(±)-Hhd→L-Ala→L-Orn→β-Ala→L-Ser→L-Ser→D-Asn→D-allo-Thr→Gly]  Formula (3) (Compound 1):

wherein (±)-Hhd represents (±)-hydroxyhexadecanoic acid; and L-Orn represents L-ornithine.

A fragment Fmoc-Gly-Hhd-OH which has been prepared beforehand and contains an ester bond is immobilized according to a known method on a resin bead commonly used for solid phase synthesis. A protected linear peptide represented by Formula (4) is then synthesized on a solid carrier such as a resin bead using a conventional automated peptide synthesizer.

H-L-Ala-L-Orn(Boc)-β-Ala-L-Ser(t-Bu)-L-Ser(t-Bu)-D-Asn-D-allo-Thr-Gly-(±)-Hhd-OH  Formula (4):

The protected linear peptide is cleaved from the resin using an appropriate known cleavage reagent, and then subjected to a cyclization reaction to obtain a protected cyclic peptide represented by Formula (5). The Compound 1 of interest which is represented by Formula (3) is finally obtained by deprotection of protecting groups of the amino acid side chain contained in the protected cyclic peptide, using an appropriate known deprotection reagent.

Cyclo[(±)-Hhd→L-Ala→L-Orn(Boc)→β-Ala→L-Ser(t-Bu)→L-Ser(t-Bu)→D-Asn→D-allo-Thr→Gly]  Formula (5):

Any commercially available resins used for peptide synthesis or combinatorial synthesis can be used as a resin for the solid phase synthetic method for a synthesis of the linear peptide of general Formula (2) Preferably, 2-chlorotritylchloride resin (Cl-Trt(2-Cl)-Resin, 100-200 mesh, 1% divinylbenzene (DVB) crosslinkage) as described in Barlos et al. (Tetrahedron Letters, 30:3947, 1989) is used.

Formation of an ester bond between $Gly^9$ and $(±)\text{-}Hhd^1$ is carried out, for example, according to a method in which a coupling agent such as PyBroP or HATU is used, preferably, a method in which dicyclohexylcarbodiimide (DCC) is used in the presence of a catalyst such as dimethylaminopyridine or 4-pyrrolidinopyridine.

A reaction for immobilization of a fragment such as Fmoc-Gly-(±)-Hhd-OH, containing an ester bond between $Gly^9$ and $(±)\text{-}Hhd^1$ synthesized as described above, onto 2-chlorotritylchloride resin (Cl-Trt(2-Cl)-Resin) is carried out in an organic solvent (e.g., dimethylformamide, tetrahydrofuran or dichloromethane) in the presence of a base (e.g., triethylamine, N-methylmorphorine or diisopropylethylamine) at a temperature of 0° C. to 50° C. Preferably, the reaction is carried out in dichloromethane using diisopropylethylamine as a base. The choice of the solvent used for the reaction gives serious influence to the immobilization yield. Then, dichloromethane which is a solvent that results in a high swelling rate of a resin is preferably selected.

Elongation of a peptide chain on a resin can be carried out according to the Fmoc method or the Boc method, which may be carried out manually or using an automated synthesizer. Preferably, the elongation is carried out according to the Fmoc method using an automated synthesizer. An exemplary protocol of peptide synthesis according to the Fmoc method using an automated peptide synthesizer is shown in FIG. 1.

The water-soluble carbodiimide (WSCD; EDC)-HOBt method, the PyBOP-HOBt method, the HATU method or the like can be used as a method for coupling of amino acids in the presence of a base such as diisopropylethylamine or N-methylmorpholine. Preferably, the coupling is carried out according to the PyBOP-HOBt method using N-methylmorpholine as a base.

Although a reaction of selective deprotection of N-Fmoc group proceeds using a wide range of bases, it is carried out using 10 to 100% piperidine, preferably a 30% piperidine/dimethylformamide solution.

After a synthesis according to the Fmoc method using an automated synthesizer is completed, a cleavage reaction of the obtained peptide from a resin is usually carried out using a solution prepared by adding anisole, thioanisole, ethanedithiol or the like as a scavenger to trifluoroacetic acid, hydrochloric acid, trifluoromethanesulfonic acid or the like. Generally, the protecting groups of amino acid side chain are also removed at the same time. If a peptide having protected amino acid is to be cleaved from a resin, the cleavage is carried out preferably using a mixture of acetic acid—trifluoroethanol—methylene chloride.

Both the amino group at the N terminus and the carboxyl group at the C terminus in the protected peptide cleaved from the resin are free groups. A cyclization between these free groups can be carried out by converting the peptide into a peptide having an activated carboxyl group at the C terminus, and then subjecting it to a reaction in the presence of a base. Generally, a temperature ranging from −30 to 60° C., preferably from −10 to 30° C. is selected as a reaction temperature for the above-mentioned cyclization reaction although it varies depending on the selected activating group of carboxyl group. The reaction time for the cyclization is ranging from several minutes to several days, preferably from 30 minutes to four hours.

In the cyclization, for example, a method of conversion into N-hydroxysuccinimide (ONSu) or a method of activation with PyBroP, HATU or DCC—HOAt can be used for activating the carboxyl group at the C terminus. DIEA, triethylamine, pyridine or the like can be used as a base. Tetrahydrofuran, methylene chloride, dimethylformamide, dimethyl sulfoxide or the like can be used as a solvent for cyclization. Dimethyl sulfoxide is preferably used in a cyclization of the linear peptide of Formula (4).

If the carboxyl group at the C terminus is to be activated with HATU, the activated peptide can be obtained by reacting the peptide of Formula (4) (i.e., one having amino group in a free or salt form at the N terminus and free carboxyl group at the C terminus) with HATU in the presence of a base in a solvent (e.g., dimethyl sulfoxide) at a temperature ranging from −10 to 30° C. In this case, the reaction proceeds accompanying cyclization. The cyclization yield can be further increased, for example, by precise control of the concentrations of the respective reaction components in the reaction mixture or the reaction temperature, or by appropriate selection of the solvent.

The compound of the present invention is prepared by cleaving a peptide having protected amino acid from a resin, carrying out a cyclization and then removing the protecting groups on the amino acid side chains using a mixture of an acid and a scavenger as described above.

Thus, the novel cyclic peptides whose minimum inhibitory concentrations (MICs, μg/ml) for *Candida albicans, Cryptococcus neoformans* and *Aspergillus fumigatus* are very low and having no toxicological effect can be obtained.

Description About Salt Form Useful as Medicine

The cyclic peptide of the present invention can be used for medicine as it is or as a pharmacologically acceptable salt thereof. There is no specific limitation concerning the salt as long as it is pharmacologically acceptable. Examples thereof include salts with mineral acids (hydrochloric acid, sulfuric acid, nitric acid, phosphoric acid, hydrofluoric acid, hydrobromic acid, etc.); organic acids (formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, etc.); and alkaline metals or alkaline earth metals (sodium, potassium, calcium, etc.).

If the cyclic peptide or a pharmacologically acceptable salt thereof of the present invention is to be administered as a medicine, it is administered as it is or as formulated into a pharmaceutical composition containing the compound, for example, at a concentration of 0.1 to 99.5%, preferably, 0.5 to 90% in a pharmaceutically acceptable, nontoxic and inert excipient to animals including humans.

Examples of excipient include solid, semisolid or liquid diluents, fillers and other formulation auxiliaries. One or more of them can be used.

It is preferable to administer the said pharmaceutical composition in a unit dosage form. The said pharmaceutical composition can be administered orally, interstitially, topically (e.g., transdermally) or transrectally. Of course, the pharmaceutical compositions should be administered in dosage forms suitable for the respective routes of administration.

The dosage as an antifungal agent of the cyclic peptide or a pharmacologically acceptable salt thereof of the present invention to be administered as a medicine should be desirably adjusted according to the conditions of the patient (age, weight, etc.), the administration route, the nature and severity of the disease and the like. Usually, the amount of the active ingredient of the present invention to be administered to an adult human is 10 to 2000 mg/day. A dosage less than the above may be sufficient in some cases, while a dosage more than the above may be required in other cases. If a large amount is to be administered, the dosage may be preferably administered in portions several times a day.

The oral administration can be carried out using a solid, powder or liquid unit dosage form such as epipastics, powders, tablets, sugar coated tablets, capsules, drops, sublingual tablets or other dosage forms.

The interstitial administration can be carried out, for example, using a liquid unit dosage form (e.g., a solution or suspension) for subcutaneous, intramuscular or intravenous injection. Such dosage forms can be prepared by suspending or dissolving a predetermined amount of the cyclic peptide or a pharmacologically acceptable salt thereof of the present invention in an injectable nontoxic liquid carrier such as an aqueous or oleaginous medium, and then sterilizing the resulting suspension or solution.

The topical administration (e.g., transdermal administration) can be carried out using an external dosage form such as liquid, cream, powder, paste, gel or ointment. Such a dosage form can be prepared by mixing a predetermined amount of the cyclic peptide or a pharmacologically acceptable salt thereof of the present invention with one or more of flavor, coloring agent, filler, detergent, humectant, emollient, gelating agent, vehicle, preservative, stabilizer and the like which are acceptable for an external dosage form.

The transrectal administration can be carried out, for example, using a suppository prepared by mixing a predetermined amount of the cyclic peptide or a pharmacologically acceptable salt thereof of the present invention with the solid having a low melting point such as higher esters (e.g., palmitic acid myristyl ester), polyethyleneglycol, cacao fat or a mixture thereof.

The physicochemical and biological properties of typical compounds according to the present invention are as follows.

(1) Physicochemical Properties

The physicochemical properties of the typical compounds 1-7 in the present invention as shown in Table 1 above are shown in Table 2 below.

TABLE 2

| Compound no. | Molecular formula | FAB-MS |
|---|---|---|
| 1 | $C_{43}H_{76}N_{10}O_{14}$ | 957 |
| 2 | $C_{43}H_{76}N_{10}O_{14}$ | 957 |
| 3 | $C_{44}H_{77}N_{11}O_{15}$ | 1000 |
| 4 | $C_{44}H_{76}N_{10}O_{16}$ | 1001 |
| 5 | $C_{45}H_{78}N_{10}O_{16}$ | 1015 |
| 6 | $C_{42}H_{74}N_{10}O_{14}$ | 943 |
| 7 | $C_{43}H_{76}N_{10}O_{15}$ | 973 |

(2) Biological Properties

The cyclic peptide of the present invention exhibits high antifungal activities on *Candida albicans, Cryptococcus neoformans* and *Aspergillus fumigatus* which are fungi typically used for determining an antifungal activity. For example, Compound 1 at a concentration of 12.5 µg/ml or less can inhibit the growth of *Candida albicans* and *Cryptococcus neoformans*.

No toxicity was observed when 100 mg/kg each of the compounds was administered intraperitoneally to mice.

EXAMPLES

The following Examples illustrate the present invention in more detail, but are not to be construed to limit the scope thereof.

Example 1

Synthesis of cyclo(-L-Ala-L-Orn-β-Ala-L-Ser-L-Ser-D-Asn-D-allo-Thr-Gly-(±)-Hhd-) (Compound 1)

1) Phenacyl (±)-3-hydroxyhexadecanoate ((±)-Hhd-OPac) (Pac: phenacyl)

To a suspension of (±)-3-hydroxyhexadecanoic acid (500 mg, 1.84 mmol) in ethyl acetate (3.6 ml) were added phenacyl bromide (421 mg, 2.12 mmol) and triethylamine (294 mg, 2.12 mmol). The mixture was stirred at room temperature overnight. The reaction mixture was washed with water, saturated aqueous sodium hydrogencarbonate and saturated aqueous sodium chloride, and then dried over magnesium sulfate. Magnesium sulfate was filtered off and the filtrate was concentrated under reduced pressure to obtain 678 mg of the title compound as a pale yellow solid.

2) Fmoc-Gly-(±)-Hhd-OPac

To a suspension of (±)-Hhd-OPac prepared in 1) above (300 mg, 0.77 mmol) in methylene chloride (2 ml) were added Fmoc-Gly-OH (274 mg, 0.92 mmol), dimethylaminopyridine (28.2 mg, 0.23 mmol) and dicyclohexylcarbodiimide (190 mg, 0.92 mmol). The mixture was stirred at room temperature overnight. Ethyl acetate was added to the reaction mixture. The mixture was washed with 10% citric acid, saturated aqueous sodium hydrogencarbonate and saturated aqueous sodium chloride, and then purified on silica gel medium pressure column chromatography (40 g, eluted with $CHCl_3$) to obtain 563 mg of the title compound as a colorless solid. FAB-MS: m/z 670[MH]+.

3) Fmoc-Gly-(±)-Hhd-OH

To a solution of Fmoc-Gly-(±)-Hhd-OPac prepared in 2) above (500 mg, 0.75 mmol) in 90% acetic acid/water (37.5 ml) were added zinc dust. The mixture was stirred at room temperature for 1.5 hours. The insoluble matter was then filtered off. Ethyl acetate was added to the filtrate. The mixture was washed with 10% citric acid, saturated aqueous sodium hydrogencarbonate and saturated aqueous sodium chloride to obtain 370 mg of the title compound.

4) Fmoc-Gly-(±)-Hhd-Trityl(2-Cl)-Resin

To a solution of Fmoc-Gly-(±)-Hhd-OH prepared in 3) above (16.5 mg, 0.03 mmol) in methylene chloride (0.5 ml) were added 2-chlorotrityl-chloride-resin (50 mg, 100-200 mesh, Watanabe Kagaku Kogyo) and diisopropylethylamine (17.4 µl, 0.09 mmol). The mixture was allowed to stand at room temperature for 30 minutes. Methanol (40 µl) was added to the reaction mixture. The resin was then collected by filtration, washed with methylene chloride, dimethylformamide, isopropyl alcohol, methanol and diethyl ether, and dried under reduced pressure.

Calculation of amount of immobilized Fmoc-Gly-(±)-Hhd-OH: A 50% piperidine/methylene chloride solution (1 ml) was added to 10 mg of the resin prepared in 4) above. The mixture was gently stirred at room temperature for 30 minutes. The reaction mixture was filtrated. The filtrate and the solvent used for washing the resin (methylene chloride) were combined and concentrated under reduced pressure. The residue was dissolved in methylene chloride (20 ml) and the solution was diluted 25 times with methylene chloride. The absorbances (A267 and A301) of the solution were measured to be 0.167 and 0.079, respectively. According to a conversion equation between the absorbance and the immobilized amounts, the amounts were calculated to be 0.48 mmol/g resin (using A267 data) and 0.51 mmol/g resin (using A301 data), respectively.

5) Fmoc-L-Ala-L-Orn(Boc)-β-Ala-L-Ser(t-Bu)-L-Ser(t-Bu)-D-Asn-D-allo-Thr-Gly-(±)-Hhd-Trtyl(2-Cl)-Resin Synthesis was carried out using 50 mg of the resin prepared in 4) above, Fmoc-D-allo-Thr-OH, Fmoc-D-Asn-OH, Fmoc-L-Ser(t-Bu)-OH, Fmoc-L-Ser(t-Bu)-OH, Fmoc-β-Ala-OH, Fmoc-L-Orn(Boc)-OH and Fmoc-L-Ala-OH (the amount of each Fmoc-amino acid used was 10 times compared with the amount of immobilized Fmoc-Gly-(±)-Hhd-OH), and an automated peptide synthesizer PSSM-8 (Shimadzu) according to a conventional protocol of automated synthesis by the PyBOP-HOBt method. After confirming the completion of the synthetic protocol, the resin was washed with isopropyl alcohol and methanol, and dried under reduced pressure.

6) H-L-Ala-L-Orn(Boc)-β-Ala-L-Ser(t-Bu)-L-Ser(t-Bu)-D-Asn-D-allo-Thr-Gly-(±)-Hhd-OH The resin obtained in 5) above was suspended in a mixture of acetic acid—trifluoroethanol—methylene chloride (1:1:8) (0.8 ml). The suspension was allowed to stand at room temperature for one hour. The resin was filtered off. The filtrate was concentrated under argon flow, and diethyl ether was then added thereto. The deposited crystals were collected by centrifugation (10,000 rpm, 5 minutes) to obtain 19.5 mg of the title compound. FAB-MS: m/z 1429[MH]+.

7) Cyclo(-L-Ala-L-Orn(Boc)-β-Ala-L-Ser(t-Bu)-L-Ser(t-Bu)-D-Asn-D-allo-Thr-Gly-(±)-Hhd-)

A solution of H-L-Ala-L-Orn(Boc)-β-Ala-L-Ser(t-Bu)-L-Ser(t-Bu)-D-Asn-D-allo-Thr-Gly-(±)-Hhd-OH obtained in 6) above (15 mg, 10.5 mmol) in dimethyl sulfoxide (5.25 ml) was added to a solution of HATU (27.9 mg, 73.5 mmol) and diisopropylethylamine (12.8 µl, 73.5 µmol) in dimethyl sulfoxide (5.25 ml), over five hours. The mixture was further stirred at room temperature for two hours, and lyophilized. FAB-MS: m/z 1411[MH]+, 1433[MNa]+.

8) Cyclo(-L-Ala-L-Orn-β-Ala-L-Ser-L-Ser-D-Asn-D-allo-Thr-Gly-(±)-Hhd-)

A mixture of trifluoroacetic acid—anisole—ethanedithiol (94:5:1) (1 ml) was added to a residue containing cyclo(-L-Ala-L-Orn(Boc)-β-Ala-L-Ser(t-Bu)-L-Ser(t-Bu)-D-Asn-D-allo-Thr-Gly-(±)-Hhd-) obtained in 7) above. The mixture was allowed to stand at room temperature for two hours. The reaction mixture was concentrated under argon flow, and ethyl ether was added thereto. The deposited crystals were collected by centrifugation (10,000 rpm, 5 minutes), re-dissolved in dimethyl sulfoxide and lyophilized to obtain the title compound. FAB-MS: m/z 957[MH]+.

Elementary analysis: theoretical (as $C_{43}H_{76}N_{10}O_{14} \cdot 2H_2O$), C: 52.00%, H: 8.12%, N: 14.13%; analytical, C: 51.96%, H: 8.15%, N: 14.10%.

Example 2

Synthesis of cyclo(-L-Ala-L-Orn-L-Ala-L-Ser-L-Ser-D-Asn-D-allo-Thr-Gly-(±)-Hhd-) (Compound 2)

The title compound was obtained according to the procedure as described in Example 1, 5) to 8) except that Fmoc-L-Ala-OH was used in place of Fmoc-β-Ala-OH in 5). FAB-MS: m/z 957[MH]+.

Example 3

Synthesis of cyclo(-L-Ala-L-Orn-L-Asn-L-Ser-L-Ser-D-Asn-D-allo-Thr-Gly-(±)-Hhd-) (Compound 3)

The title compound (4.8 mg) was obtained according to the procedure as described in Example 1, 5) to 8) except that Fmoc-L-Asn-OH was used in place of Fmoc-β-Ala-OH in 5). FAB-MS: m/z 1000[MH]+.

Example 4

Synthesis of cyclo(-L-Ala-L-Orn-L-Asp-L-Ser-L-Ser-D-Asn-D-allo-Thr-Gly-(±)-Hhd-) (Compound 4)

The title compound was obtained according to the procedure as described in Example 1, 5) to 8) except that Fmoc-L-Asp-OH was used in place of Fmoc-β-Ala-OH in 5). FAB-MS: m/z 1001[MH]+.

Example 5

Synthesis of cyclo(-L-Ala-L-Orn-L-Glu-L-Ser-L-Ser-D-Asn-D-allo-Thr-Gly-(±)-Hhd-)(Compound 5)

The title compound was obtained according to the procedure as described in Example 1, 5) to 8) except that Fmoc-L-Glu-OH was used in place of Fmoc-β-Ala-OH in 5). FAB-MS: m/z 1015[MH]+.

Example 6

Synthesis of cyclo(-L-Ala-L-Orn-Gly-L-Ser-L-Ser-D-Asn-D-allo-Thr-Gly-(±)-Hhd-) (Compound 6)

The title compound was obtained according to the procedure as described in Example 1, 5) to 8) except that Fmoc-Gly-OH was used in place of Fmoc-β-Ala-OH in 5). FAB-MS: m/z 943[MH]+.

Example 7

Synthesis of cyclo(-L-Ala-L-Orn-L-Ser-L-Ser-L-Ser-D-Asn-D-allo-Thr-Gly-(±)-Hhd-) (Compound 7)

The title compound was obtained according to the procedure as described in Example 1, 5) to 8) except that. Fmoc-L-Ser(t-Bu)-OH was used in place of Fmoc-β-Ala-OH in 5). FAB-MS: m/z 973[MH]+.

Example 8

Determination of Antifungal Activities

The antifungal activities of the compounds synthesized in Examples 1 and 3 to 7 were measured by a liquid medium dilution method.

*Candida albicans* TIMM0136, *Cryptococcus neoformans* TIMM0354 or *Aspergillus fumigatus* TIMM1776 was inoculated into a medium containing one of the compounds diluted serially, and cultured at 30° C. for two days. The concentration at which the growth of the fungus was almost completely inhibited was defined as a minimum inhibitory concentration (MIC, μg/ml). For the measurements, a medium containing 0.67% Yeast Nitrogen Base (Difco) and 1.0% glucose (YNBG medium) was used for the cultures of *Candida albicans* and *Cryptococcus neoformans*, and a medium containing 0.5% Brain Heart Infusion Bouillon (Nissui) (BHI medium) was used for the culture of Aspergillus fumigatus. The results are shown in Table 3.

As shown in Table 3, Compounds 1, 3, 4, 5, 6 and 7 exhibited high antifungal activities on *Candida albicans* (C.a.), *Cryptococcus neoformans* (C.n.) and *Aspergillus fumigatus* (A.f.).

TABLE 3

| Compound | MIC (μg/ml) | | |
| --- | --- | --- | --- |
| | C.a. | A.f. | C.n. |
| 1 | 6.25 | 1.56 | 12.5 |
| 3 | 6.25 | 1.56 | 3.12 |
| 4 | 6.25 | — | 6.25 |
| 5 | 3.12 | 0.39 | 6.25 |
| 6 | 12.5 | — | 3.12 |
| 7 | 6.25 | 0.78 | 3.12 |

Example 9

Synthesis of Analogs of Compound 1 Having Substitution of L-Thr or D-Thr for D-allo-Thr in $AA^7$, cyclo(-L-Ala-L-Orn-β-Ala-L-Ser-L-Ser-D-Asn-$AA^7$-Gly-(±)-Hhd-), and Comparison of Antifungal Activities Thereof 1) Synthesis of the $AA^7$:L-Thr-Substituted Analog A compound having substitution of L-Thr in $AA^7$ in the compound 1 (the $AA^7$:L-Thr-substituted analog) was obtained according to the procedure as described in Example 1, 5) to 8) except that Fmoc-L-Thr(tBu)-OH was used in place of Fmoc-D-allo-Thr-OH in 5). FAB-MS: m/z 957[MH]+.

2) Synthesis of the $AA^7$:D-Thr-Substituted Analog

A compound having substitution of D-Thr in $AA^7$ in the compound 1 (the $AA^7$:D-Thr-substituted analog) was obtained according to the procedure as described in Example 1, 5) to 8) except that Fmoc-D-Thr(t-Bu)-OH was used in place of Fmoc-D-allo-Thr-OH in 5). FAB-MS: m/z 957[MH]+.

3) Comparison of Antifungal Activities

The antifungal activities of the $AA^7$:L-Thr-substituted analog and the $AA^7$:D-Thr-substituted analog against *Candida albicans, Cryptococcus neoformans* and *Aspergillus fumigatus* were measured as described in Example 8. As shown in Table 3, the compound having D-allo-Thr without substitution in $AA^7$ (Compound 1) showed antifungal activities against *Candida albicans, Cryptococcus neoformans* and *Aspergillus fumigatus* with MICs of 6.25 μg/ml, 12.5 μg/ml and 1.56 μg/ml, respectively. The $AA^7$:L-Thr-substituted analog or the $AA^7$:D-Thr-substituted analog did not show the activity against any of the fungi (MIC>200 μg/ml).

Example 10

Preparation of a Mixture of $AA^4$-Substituted Analogs, cyclo(-L-Ala-L-Orn-β-Ala-$AA^4$-L-Ser-D-Asn-D-allo-Thr-Gly-(±)-Hhd-)

A mixture of twenty title cyclic peptides each having one of L-Ala, L-Arg, L-Asn, L-Asp, L-Cys, L-Gln, L-Glu, L-Gly, L-His, L-Ile, L-Leu, L-Lys, L-Met, L-Phe, L-Pro, L-Ser, L-Thr, L-Trp, L-Tyr and L-Val at $AA^4$ of Compound 1 was prepared.

A synthetic protocol was carried out according to the procedure as described in Example 1, 5) to 8) except that a mixture of 1/20 amounts (moles) each of Fmoc-L-Ala-OH, Fmoc-L-Arg(Pmc)-OH, Fmoc-L-Asn(Trt)-OH, Fmoc-L-Asp (Ot-Bu)-OH, Fmoc-L-Cys(Trt)-OH, Fmoc-L-Gln(Trt)-OH, Fmoc-L-Glu(Ot-Bu)-OH, Fmoc-L-Gly-OH, Fmoc-L-His(Trt)-OH, Fmoc-L-Ile-OH, Fmoc-L-Leu-OH, Fmoc-L-Lys(Boc)-OH, Fmoc-L-Met-OH, Fmoc-L-Phe-OH, Fmoc-L-Pro-OH, Fmoc-L-Ser(t-Bu)-OH, Fmoc-L-Thr(t-Bu)-OH, Fmoc-L-Trp-OH, Fmoc-L-Tyr(t-Bu)-OH and Fmoc-L-Val-OH than Fmoc-L-Ser(t-Bu)-OH was used in place of Fmoc-L-Ser(t-Bu)-OH used for the $AA^4$ amino acid in Example 1, 5). From the FAB-MS spectrum of the finally obtained residue, it was confirmed that the twenty title cyclic peptides were obtained.

Example 11

Preparation of a Mixture of $AA^5$ Amino Acid-Substituted Analogs, cyclo(-L-Ala-L-Orn-β-Ala-L-Ser-$AA^5$-D-Asn-D-allo-Thr-Gly-(±)-Hhd-)

A mixture of twenty title cyclic peptides each having one of L-Ala, L-Arg, L-Asn, L-Asp, L-Cys, L-Gln, L-Glu, L-Gly, L-His, L-Ile, L-Leu, L-Lys, L-Met, L-Phe, L-Pro, L-Ser, L-Thr, L-Trp, L-Tyr and L-Val at $AA^4$ of Compound 1 was prepared.

A synthetic protocol was carried out according to the procedure as described in Example 1, 5) to 8) except that a mixture of 1/20 amounts (moles) each of Fmoc-L-Ala-OH, Fmoc-L-Arg(Pmc)-OH, Fmoc-L-Asn(Trt)-OH, Fmoc-L-Asp(Ot-Bu)-OH, Fmoc-L-Cys(Trt)-OH, Fmoc-L-Gln(Trt)-OH, Fmoc-L-Glu(Ot-Bu)-OH, Fmoc-L-Gly-OH, Fmoc-L-His(Trt)-OH, Fmoc-L-Ile-OH, Fmoc-L-Leu-OH, Fmoc-L-Lys(Boc)-OH, Fmoc-L-Met-OH, Fmoc-L-Phe-OH, Fmoc-L-Pro-OH, Fmoc-L-Ser(t-Bu) —OH, Fmoc-L-Thr(t-Bu)-OH, Fmoc-L-Trp-OH, Fmoc-L-Tyr(t-Bu)-OH and Fmoc-L-Val-OH than Fmoc-L-Ser(t-Bu)-OH was used in place of Fmoc-L-Ser(t-Bu)-OH for introducing the $AA^5$ amino acid in 5). The FAB-MS spectrum of the finally obtained residue was analyzed to confirm that the twenty title cyclic peptides were contained.

Example 12

Preparation of a Mixture of AA6 Amino Acid-Substituted Analogs, cyclo(-L-Ala-L-Orn-β-Ala-L-Ser-L-Ser-$AA^6$-D-allo-Thr-Gly-(±)-Hhd-)

A mixture of thirteen title cyclic peptides each having one of D-Ala, D-Asn, D-Asp, D-Glu, D-His, D-Ile, D-Leu, D-Phe, D-Ser, D-Thr, D-Trp, D-Tyr and D-Val at $AA^6$ of Compound 1 was synthesized.

A synthesis protocol was carried out according to the procedure as described in Example 1, 5) to 8) except that a mixture of 1/13 amounts (moles) of Fmoc-D-Ala-OH, Fmoc-D-Asn(Trt)-OH, Fmoc-D-Asp(Ot-Bu)-OH, Fmoc-D-Glu (Ot-Bu)-OH, Fmoc-D-His(Trt)-OH, Fmoc-D-Ile-OH, Fmoc-D-Leu-OH, Fmoc-D-Phe-OH, Fmoc-D-Ser(t-Bu)-OH, Fmoc-D-Thr(t-Bu)-OH, Fmoc-D-Trp-OH, Fmoc-D-Tyr(t-Bu)-OH and Fmoc-D-Val-OH was used in place of Fmoc-D-Asn(Trt)-OH for introducing the $AA^6$ amino acid in Example 1, 5). The FAB-MS spectrum of the finally obtained residue was analyzed to confirm that the thirteen title cyclic peptides were contained.

Example 13

Antifungal Activities of Mixtures of $AA^4$, $AA^5$ or $AA^6$ Amino Acid-Substituted Analogs of Compound 1

The antifungal activities of the mixtures of $AA^4$, $AA^5$ or $AA^6$ amino acid-substituted analogs obtained in Examples 10, 11 and 12 against *Candida albicans, Cryptococcus neoformans* and *Aspergillus fumigatus* were measured as described in Example 8. The mixture of $AA^4$ amino acid-substituted analogs exhibited activities on *Cryptococcus neoformans* and *Aspergillus fumigatus* with MICs of 100 μg/ml and 50 μg/ml, respectively. The mixture of $AA^5$ amino acid-substituted analogs exhibited antifungal activities on *Candida albicans, Cryptococcus neoformans* and *Aspergillus fumigatus* with MICs of 25 μg/ml, 50 μg/ml and 25 μg/ml, respectively. The mixture of $AA^6$ amino acid-substituted analogs exhibited antifungal activities on *Candida albicans, Cryptococcus neoformans* and *Aspergillus fumigatus* with MICs of 50 μg/ml, 50 μg/ml and 25 μg/ml, respectively.

The invention claimed is:
1. The cyclic peptide represented by general formula (I) or a pharmacologically acceptable salt thereof:

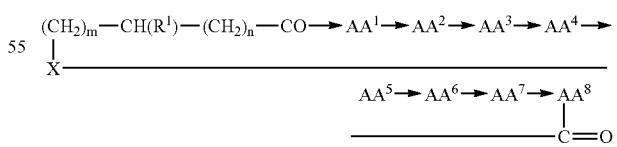

Wherein:
  m and n may be identical or different from each other, and are independently 0 or 1;
  X is O or NH;
  $R^1$ is $CH_3(CH_2)_{12}$-, $CH_3(H_2)_{10}CONH$— or $CH_3(CH_2)_{10}COCH_2$- ;
  $AA^1$ is L-alanine;

AA² is L-ornithine;
AA³ is β-alanine, glycine, L-alanine, L-asparagine, L-aspartic acid, L-glutamic ancid, L-serine or D-allo-threonine;
AA⁴ is L-serine or D-allo-threonine;
AA⁵ is L-serine or D-allo-threonine;
AA⁶ is D-asparagine;
AA⁷ is D-allo-threonine, D-β-hydroxyvaline or D-β-hydroxyphenyl alanine; and
AA⁸ is glycine or D-allo-threonine.

2. An antifungal pharmaceutical composition which contains the cyclic peptide or a pharmacologically acceptable salt thereof defined by claim 1.

3. The cyclic peptide represented by general formula (I) or a pharmacologically acceptable salt thereof according to claim 1, wherein:

m is 0;
n is 1;
X is 0;
$R^1$ is $CH_3(CH_2)_{12}^-$;
AA¹ is L-alanine;
AA² is L-ornithine;
AA³ is β-alanine, glycine, L-alanine, L-asparagine, L-aspartic acid, L-glutamic acid, L-serine or D-allo-threonine;
AA⁴ is L-serine;
AA⁵ is L-serine;
AA⁶ is D-asparagine;
AA⁷ is D-allo-threonine; and
AA⁸ is glycine.

* * * * *